United States Patent [19]
Matsushima

[11] Patent Number: 5,387,254
[45] Date of Patent: Feb. 7, 1995

[54] HUMIDITY MEASURING DEVICE AND A HEAT COOKER EMPLOYING THE DEVICE

[75] Inventor: Haruo Matsushima, Yamatokoriyama, Japan

[73] Assignee: Matsushita Electric Industrial Co., Ltd., Osaka, Japan

[21] Appl. No.: 27,076

[22] Filed: Mar. 5, 1993

[30] Foreign Application Priority Data

Mar. 6, 1992 [JP] Japan ................. 4-049230
May 11, 1992 [JP] Japan ................. 4-117118

[51] Int. Cl.[6] ........................................... G01N 29/02
[52] U.S. Cl. ........................... 73/24.04; 73/335.02
[58] Field of Search ............ 73/29.01, 335.02, 24.01, 73/24.04

[56] References Cited

U.S. PATENT DOCUMENTS 4,255,964  3/1981  Morison ..................... 73/24.01
4,876,889 10/1989  Shakkottai et al. ......... 73/335.02 X

FOREIGN PATENT DOCUMENTS 1250933  8/1986  U.S.S.R. ................. 73/335.02
1290154  2/1987  U.S.S.R. ................. 73/335.02

Primary Examiner—Hezron E. Williams
Assistant Examiner—Joseph W. Roskos
Attorney, Agent, or Firm—Cornelius F. O'Brien

[57] ABSTRACT

The present invention relates to a highly reliable, accurate humidity measuring device which detects differences in humidity between datum air and measuring air as a time or a phase difference in the propagation velocity of ultrasonic waves, using ultrasonic wave generating and receiving means, and processes this difference using circuitry.

17 Claims, 8 Drawing Sheets

HUMIDITY MEASURING DEVICE AND A HEAT COOKER EMPLOYING THE DEVICE

FIELD OF THE INVENTION

The present invention relates in one aspect to a humidity measuring device which detects differences in humidity between datum air and measuring air as a time or a phase difference in the propagation velocity of ultrasonic waves, using ultrasonic wave generating and receiving means, and processes this difference using circuitry, and in another aspect to a heating cooker equipped with aforesaid humidity measuring device, which detects the cooking condition of food by measuring humidity changes due to the steam generated from food using aforesaid humidity measuring device, and controls or shuts off the heat source.

BACKGROUND OF THE INVENTION

Description of the Conventional Technique

Conventionally, a microwave oven, which is one example of a heat cooker, uses a humidity sensor with a semiconductor to detect cooking conditions and to control the heat source. In this example, the steam from the food which is heated dielectrically bonds to the semiconductor element in the humidity sensor, and the source of the electromagnetic waves is either controlled or shut off by the electric signal generated by the element. However, this system had a reliability problem when cooking food due to oil and meat juice particles, not just the steam from food, which polluted the semiconductor. Even when periodically a burning process of this pollutant was attempted using a heater or the like, the electric signal from the sensor gradually changed, possibly becoming the cause for its deterioration or malfunction.

In contrast to a humidity sensor with a semiconductor to detect humidity in the air, a method of measuring humidity by sonic waves is known, which was reported in the Kohkai Sho 48-34585. This method utilizes the characteristics that if there is a constant temperature, the velocity of the sonic waves going through the atmosphere becomes higher as the humidity becomes higher. This method of measuring humidity solves the problem of sensor pollution. However, there is a problem of measuring the humidity under the condition when the temperature change is substantial, such as in a cooker, because the velocity change of the sonic waves is more affected by the temperature change than the humidity change.

SUMMARY OF THE INVENTION

One of the objectives of the present invention is to provide a humidity measuring device with high precision and reliability, wherein the space is divided into two, and an ultrasonic wave generator is equipped and transmits to both spaces simultaneously. The sonic wave receiving means of the same characteristics are placed at an equal distance from the sonic wave generator in the both spaces. The humidity difference between datum air in one chamber and measuring air in the other chamber is detected as the velocity difference of ultrasonic waves transmitted from aforementioned ultrasonic wave generator to each said receiver. Furthermore, this difference is processed using circuitry.

Another objective of the present invention is to provide a cooker equipped with aforementioned measuring device, which detects the condition of the food by measuring the humidity change caused by the steam produced by the food using aforementioned measuring device, and controlling or shutting off the heat source, such as the electromagnetic wave generator in a microwave oven.

DESCRIPTION OF THE PREFERRED EMBODIMENTS

Figure 1A:
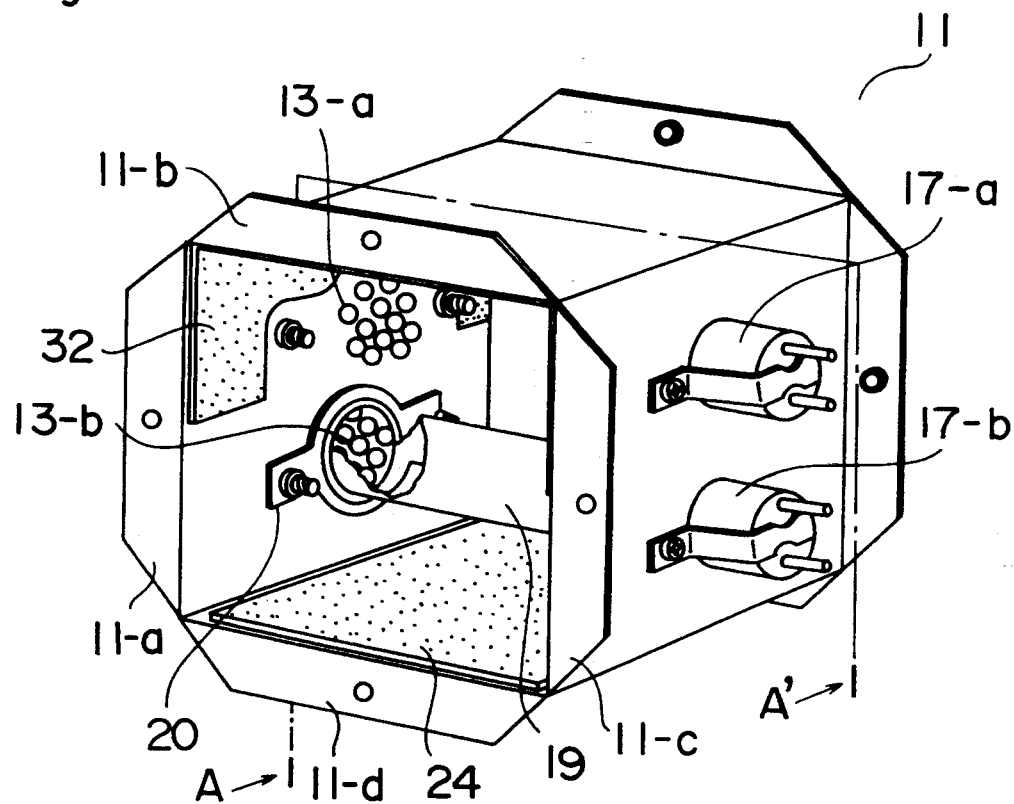
FIG. 1A is a perspective view of the humidity measuring device of the present invention in the example.
Figure 1B:
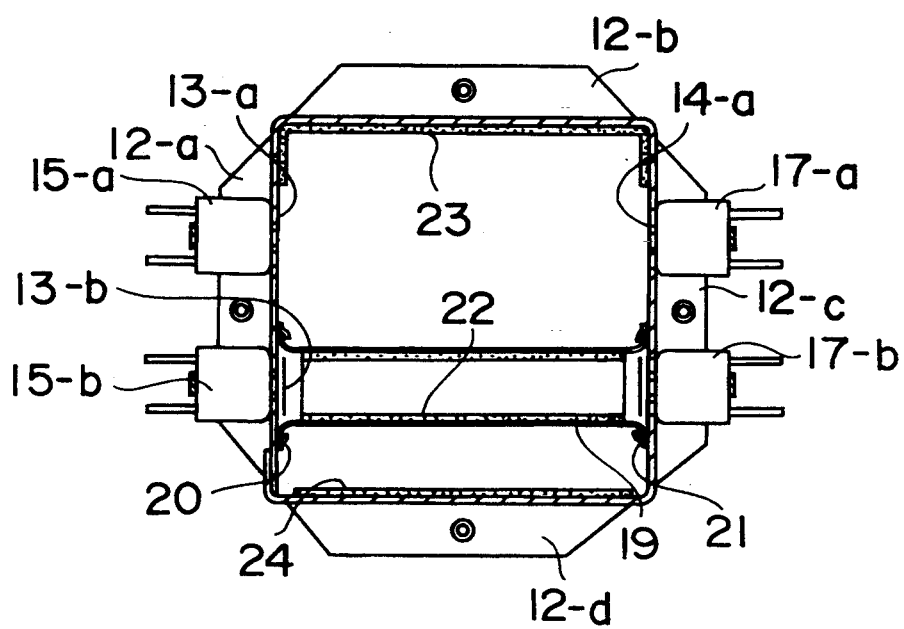
FIG. 1B is a cross sectional view of section A—A' shown in FIG. 1A.

FIG. 1A is a perspective view of one example of the humidity measuring device of the present invention when it was placed in the exhaust passage of the cooker and FIG. 1B is a cross section of view A—A'.

The exhaust passage is of a square pipe shape 11 made of thin stainless steel, bent approximately 10 mm in width at both the top and bottom of the same planes (front and rear in FIG. 1A) designated 11-$a$, 11-$b$, 11-$c$ and 11-$d$. The opposite side is similarly bent designated 12-$a$, 12-$b$ 12-$c$ and 12-$d$ on the same plane.

Both the right and left side of said square pipe have groups of small holes 13-$a$ and 13-$b$ (left side) and 14-$a$ and 14-$b$ (right side) within an approximate circle.

The right and left sides of said square pipe are parallel to each other, and 13-$a$ and 14-$a$, and 13-$b$ and 14-$b$ face each other respectively. Ultrasonic generating elements, 15-$a$ and 15-$b$, which are calibrated to the same frequency at approximately 40 kHz are installed on the outside of the groups of holes on the left side of the square pipe using two screws each. Ultrasonic generating elements, 17-$a$ and 17-$b$, which are calibrated to the same frequency at approximately 40 kHz are installed on the outside of the groups of holes on the right side of the square pipe using two screws each.

A thin aluminum cylindrical hollow pipe 19 of slightly larger diameter than the area of a group of small holes are placed in between said groups of small holes 13-$b$ and 14-$b$ inside the square pipe.

Although a round cylindrical pipe is shown in the example, the shape can vary.

Figure 2A:
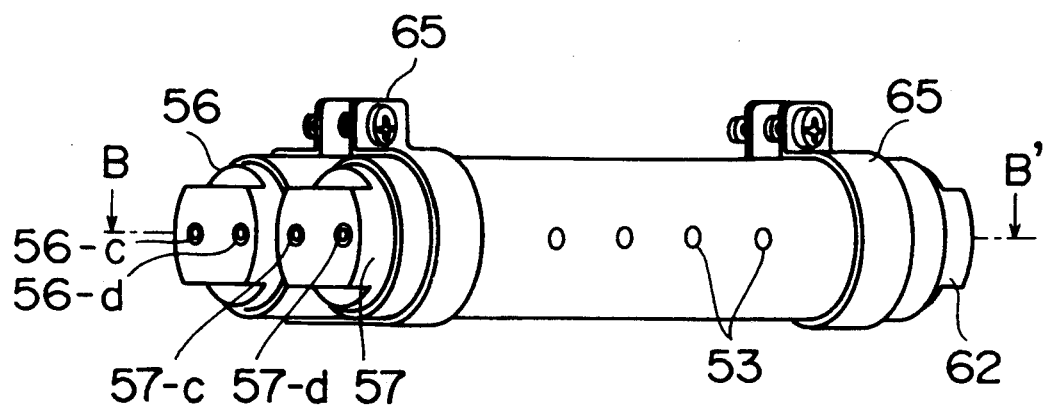
FIG. 2A is a perspective view of the humidity measuring device of the present invention in another example.
Figure 2B:
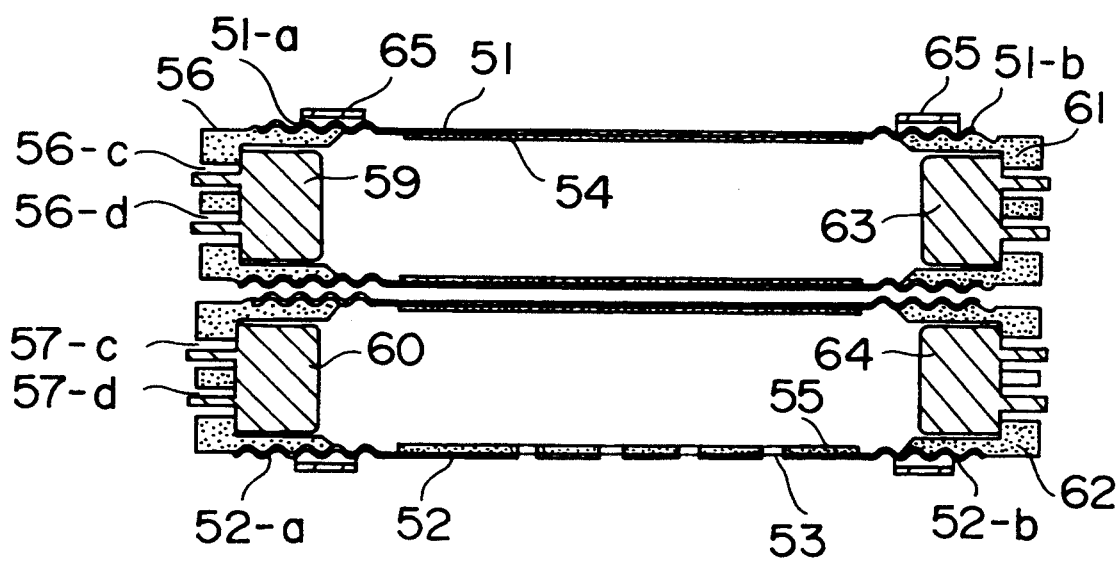
FIG. 2B is a cross sectional view of the humidity measuring device of the present invention in another example shown in FIG. 2A.

Each side of cylindrical pipe 19 hardly makes contact with the right and left interior walls of said square pipe, and the round pipe is fastened with no gaps in the left and right interior walls using flanges 20 and 21 with holes in the tabs and a hole which is slightly larger than that of aforesaid pipe. Sound absorber 22 made of polyurethane foam or the like is bonded inside pipe 19. Likewise the sound absorber 23 is installed on the interior surface of the top and part of the right and left interior walls of the square pipe, and sound absorber 24 is installed on the bottom. FIG. 2A is other example of the present invention. In particular, it is a perspective view and FIG. 2B is a cross sectional view of B—B' when used in a humidity measuring device. Hollow materials 51 and 52 are made of thin aluminum round pipes, and they are identical, with the exception of 52 having a small hole 53 on the side wall. Right-threads 51-a and 52-a are formed directly onto the interior walls of one end of the hollow materials 51 and 52, and left-threads 51-b and 52-b are formed likewise at the other end. Sound insulators 54 and 55 made of poly-urethane foam or the like are inserted into the inside of hollow materials 51 and 52.

Resin holders 56 and 57 for ultrasonic generating elements are cylindrical containers, and the bottoms of the containers are partially cut out to form a U-shape. Furthermore, the other part of the outer rims are threaded to match aforesaid right-thread 51-a and 52-a. Piezoelectrically ultrasonic generating elements 59 and 60 calibrated to the same frequency of approximately 40 kHz are installed inside the containers. Lead lines for the elements go through holes 56-c, 56-d, 57-c, and 57-d at the bottom of the containers. The holes are closed and the lead lines are secured by bonding after the lead lines go through the holes, and holders 56 and 57 for the generating elements are inserted by turning them clockwise into right-threads 51-a and 52-a of the hollow materials respectively.

Resin holders 61 and 62 for the receiving elements are exactly the same as the holders for the generating elements, except that they are threaded to match aforesaid left-thread 51-b and 52-b, and piezoelectrically ultrasonic receiving elements 63 and 64 with the same characteristics and resonating frequency of approximately 40 kHz are installed inside the containers.

In addition, two hollow materials 51 and 52 are secured in contact with each other using metal bands 65 and two sets of screws, after adjusting the distance between the generating elements and the receiving elements. (the drawing of the cross sectional view of the two materials shows the materials not touching each other for easier viewing purposes)

Figure 3:
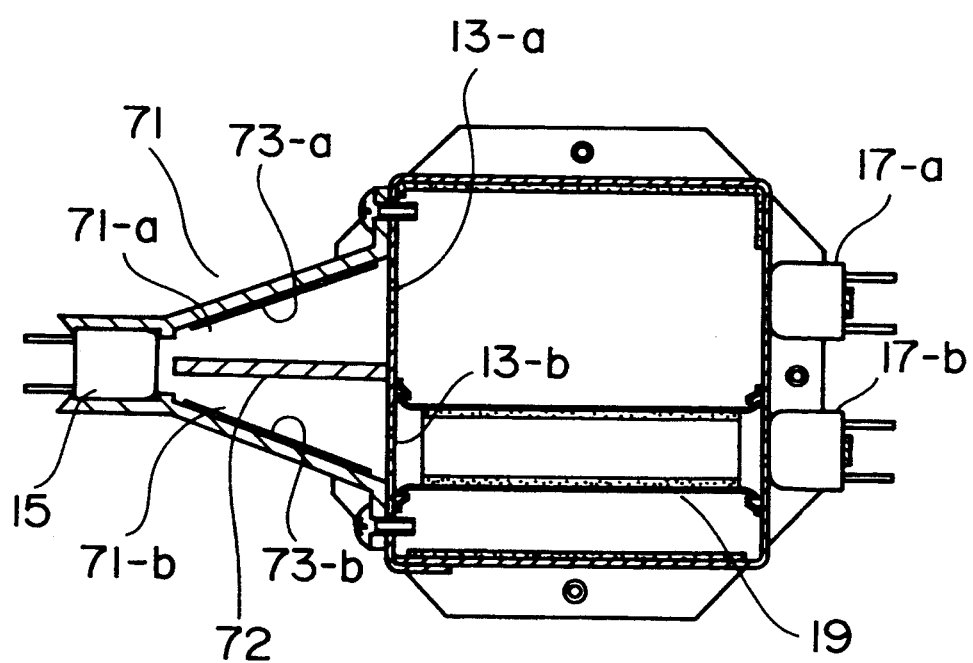
FIG. 3 is a cross sectional view of a humidity measuring device of the present invention in another example.

In FIG. 3, a passage 71 is made of resin, and has a cone shaped hollow construction. Ultrasonic generating element 15 is secured near the top of the cone, and the flat bottom of the cone should be large enough to cover both groups of holes 13-a and 13-b. Separator 72 is placed between the two groups of small holes, and extends from near the ultrasonic generating element 15 to the bottom, dividing passage 71 into two symmetric passages, 71-a and 71-b, with separator 72 as the axis of symmetry.

Passage 71 is symmetric with separator 72, an axis of symmetry. Sounds absorbers 73-a and 73-b are bonded on to passages 71-a and 71-b respectively, and the passages are secured to exhaust passage 11 with two screws.

Figure 4:
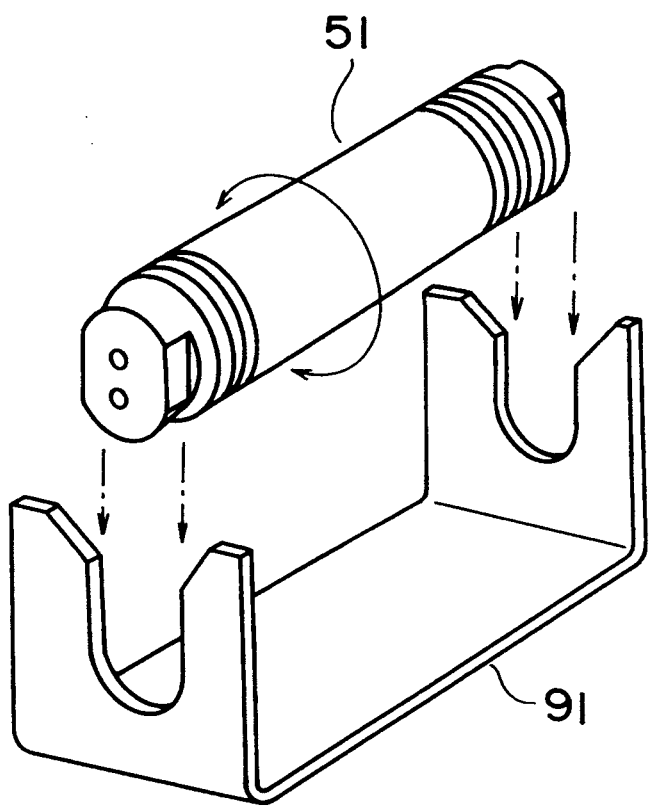
FIG. 4 is a perspective view of the adjustment work being done in the FIG. 2 example.

FIG. 4 is a perspective view to describe the adjustment in distance between the ultrasonic generating elements 59 and 60 and the corresponding receiving elements 63 and 64, respectively shown in FIG. 2B. Adjuster 91 has a U-shaped cut-out on each end. The width of the U should be slightly larger than that of the U-shape on the bottom of the container for said generating and receiving element holders. Each end should be bent at a 90° angle and be parallel to each other. The holder for the generating element is inserted into one U-shaped cut-out, and the holder for the receiving element is inserted into the other U-shaped cut-out. The distance adjustment is made by turning the cylindrical hollow materials 51 or 52.

Figure 5A:
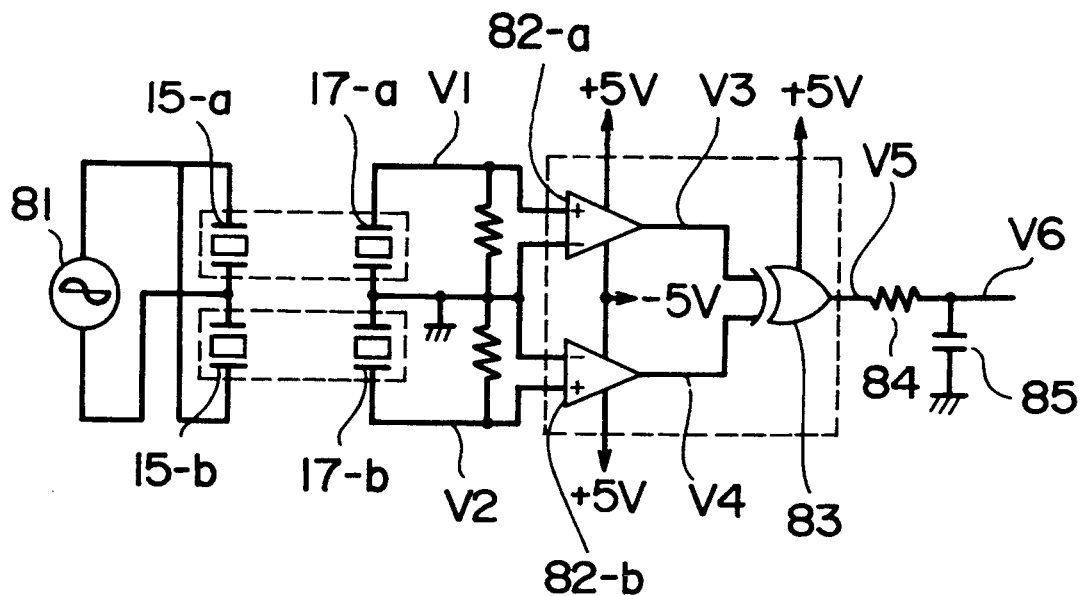
FIG. 5A is the voltage waves of electronic circuitry and other major parts employed in the humidity measuring device of the present invention.

FIG. 5 is the electronic circuit and waves of each part in the examples of the present invention. This electronic circuitry is combined with the examples in FIGS. 1A, 1B, 2A and 2B.

For example, the output for generating element 81 with a frequency of 40 kHz is connected to two ultrasonic generating elements, 15-a and 15-b (in the case of FIG. 2B, connected to 59 and 60). Outputs for the two ultrasonic receiving elements 17-a and 17-b (63 and 64 in FIG. 2B) are connected to the comparators 82-a and 82-b, and two outputs from the comparators, which are connected to the electric power source, are connected to an exclusive OR circuit 83. These outputs are connected to integrated circuit 86, which consists of resistor 84 and capacitor 85.

The output signal wave, shown in 5B, of the ultrasonic receiving element 17-a is referred to as V1; that of 17-b as V2; that of comparator 82-a as V3; that of 82-b as V4; and that of the exclusive OR circuit 83 as V5, with integrated circuit 86 being V6. To explain the effect of aforesaid device, ultrasonic waves of the same frequency and phase are generated due to output from generator 81 being added to two ultrasonic generating elements 15-a and 15-b (or 59 and 60). These ultrasonic waves intersect at exhaust passage 11, and reach ultrasonic receiving elements 17-a and 17-b (or 63 and 64). Because the distances between both generating elements and receiving elements are the same, if the temperature and humidity inside and outside the cylindrical hollow material 19 are the same, then both receiving signals should be in the same phase. Hypothetically, the temperature is the same, but if the humidities inside and outside the hollow material 19 are different from each other, then a phase difference corresponding to the humidity difference will occur.

In general, the sound velocity $C_W$ in the air of atmospheric pressure H with the steam of pressure P is acquired from sound velocity C in the dry air of the same temperature using the following formula:

$$C_W = c/\sqrt{\{1 - P/H(\gamma w/\gamma a - 0,622)\}}$$

Where $\gamma w$ denotes the ratio of specific heat at a constant pressure and specific heat at a constant volume of the steam, and likewise $\gamma a$ denotes the ratio of specific heat at a constant pressure and specific heat at a constant volume of the dry air. As is generally known, variation in the sound velocity due to a temperature change is proportional to the square root of the absolute temperature.

Figure 6:
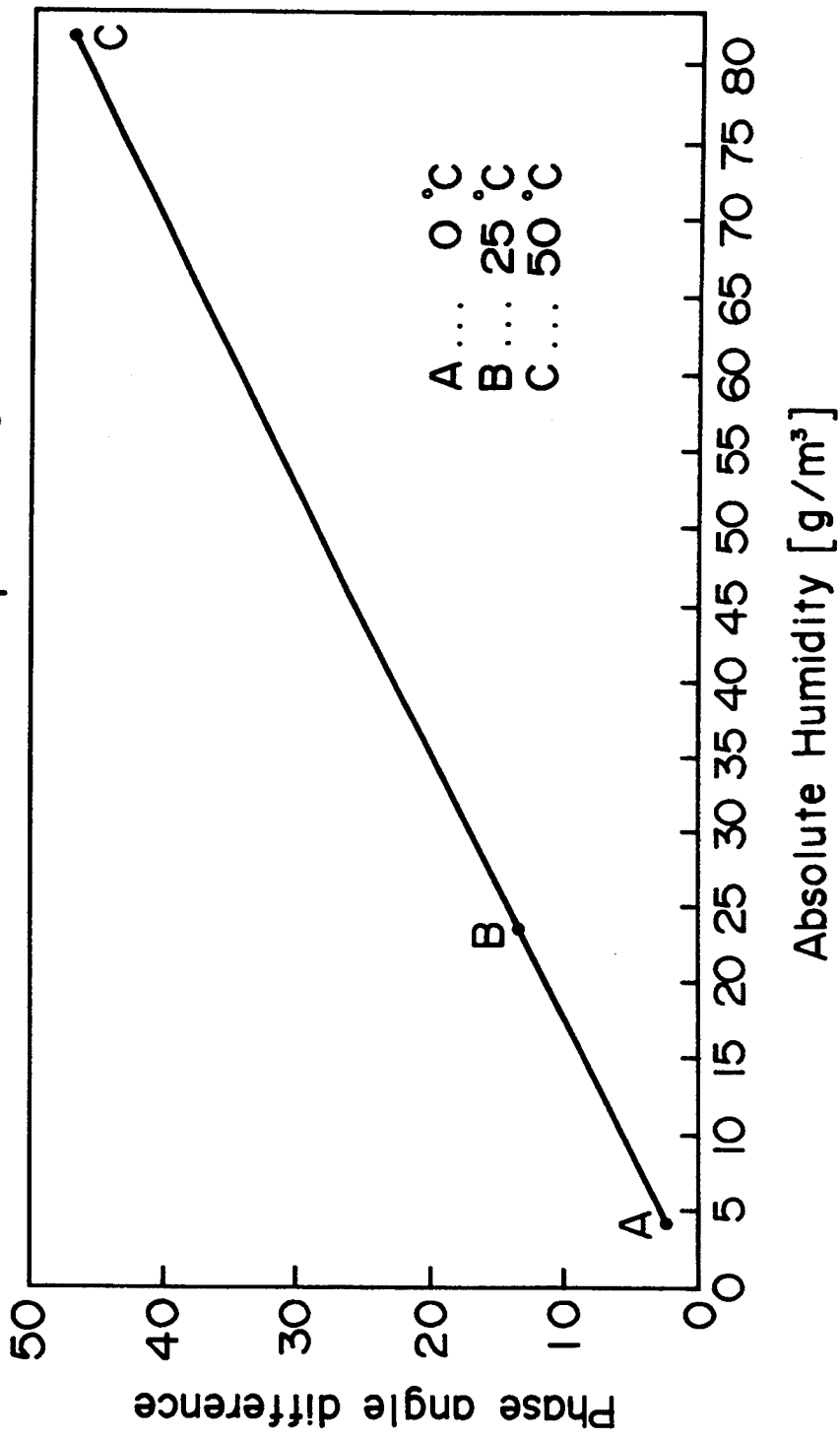
FIG. 6 is a graph indicating the correlation between the absolute humidity and phase difference in the examples in FIGS. 1 and 5.

FIG. 6 indicates the correlation between absolute humidity [g/m$^3$] and the phase angle difference at three different temperatures of 0° C., 25° C. and 50° C. In the example in FIG. 1, hypothetically the frequency is 40 kHz and the distance between the generator and receiver is 6 cm.

Since the saturated absolute humidities [g/m$^3$] are 4.85 at 0° C., 23.05 at 25° C. and 82.8 at 50° C., which are plotted as A, B and C respectively, they are linear within that range.

As this example indicates, if there is a humidity difference between the interior and exterior of hollow material 19, then a difference in receiving the signal waves between the two ultrasonic wave receiving elements 17-a and 17-b will occur.

Figure 5B:
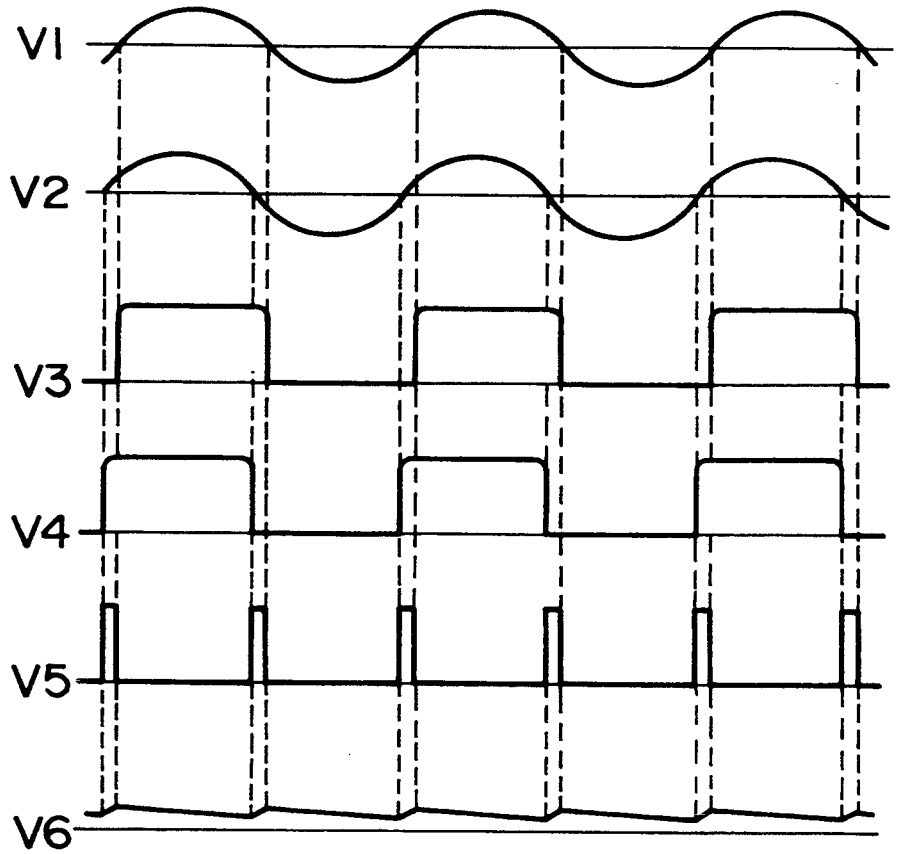
FIG. 5B is the output sine waves of circuit shown in FIG. 5A.

In other words, the shapes of the waves V1 and V2 for 17-a and 17-b show a phase difference as indicated in FIG. 5B. When this phase difference information is conveyed to the comparator, then only the rectangular waves V3 and V4 corresponding to the positive side of V1 and V2 are output. When these two are added to the exclusive OR circuit rectangular waves, V5, which only corresponds to the area where V3 and V4 do not overlap, is output. Thus, V5 is a rectangular wave which has exactly the same phase difference width for V1 and V2. When this information is conveyed to the integrated circuit, direct current voltage V6 proportional to the width of V5 is acquired.

Figure 7:
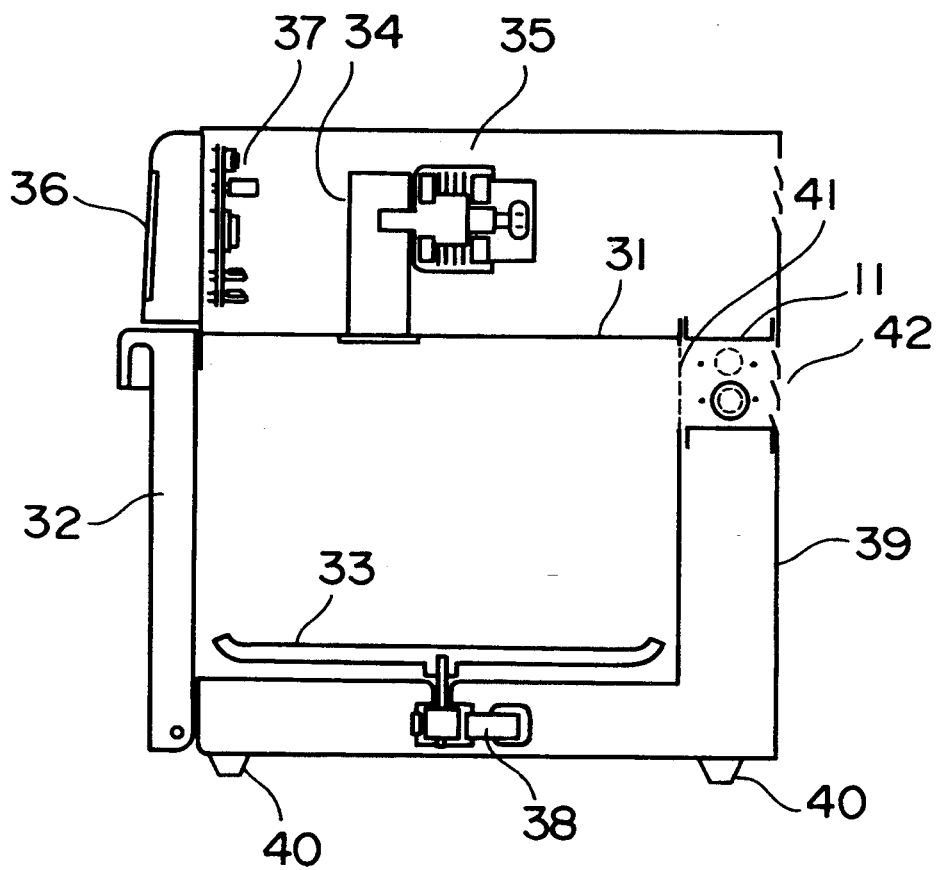
FIG. 7 is a cross sectional view of the main parts of the cooker in the present invention.

The microwave oven shown in FIG. 7 contains door 32, plate 33, display panel 36, circuitry 37, heating element 34-35, top wall 31, back wall 39, motor element 38, and support legs 40. In the microwave oven when food is heated in a heating chamber, steam is generated, and the steam is exhausted through a group of small holes 41 located in the back of the heating chamber, exhaust passage 11 and a group of louvers located in the back of the exterior box. When the steam goes through exhaust passage 11, there is a humidity difference between the interior and exterior of hollow material 19, since the steam only passes the exterior of the cylindrical hollow material 19. This difference, as aforementioned, is converted into direct voltage, and added to the control measure as humidity information.

As indicated in FIG. 3, an example with an omission of one sonic wave generating element works as well. In this case, the possibility of the steam from food entering the inside of hollow material 19 through a group of 13-a and 13-b when passing the exhaust passage may be a concern. However, in actuality, as long as the exhaust resistance of the group of louvers 42 is controlled under the resistance of a group of small holes 13-a this effect need not be of concern.

In addition, when the chamber condition is either low in both temperature and humidity or high in both temperature and humidity one concern is that the information on steam generated from food may vary substantially. However, the humidity variance in the steam from food is significantly large, thus, there is no effect on acquiring information.

For example, hypothetically if 150 g of cauliflower is heated for 2 minutes, and 7 grams of water is evaporated in a heating chamber of 20 liters, then the accumulated absolute humidity for 2 minutes is 350 g/m$^3$ compared to the absolute humidity in a high temperature and humidity atmosphere of 30° C. with 100% relative humidity being 30.3 g/m$^3$.

Figure 8:
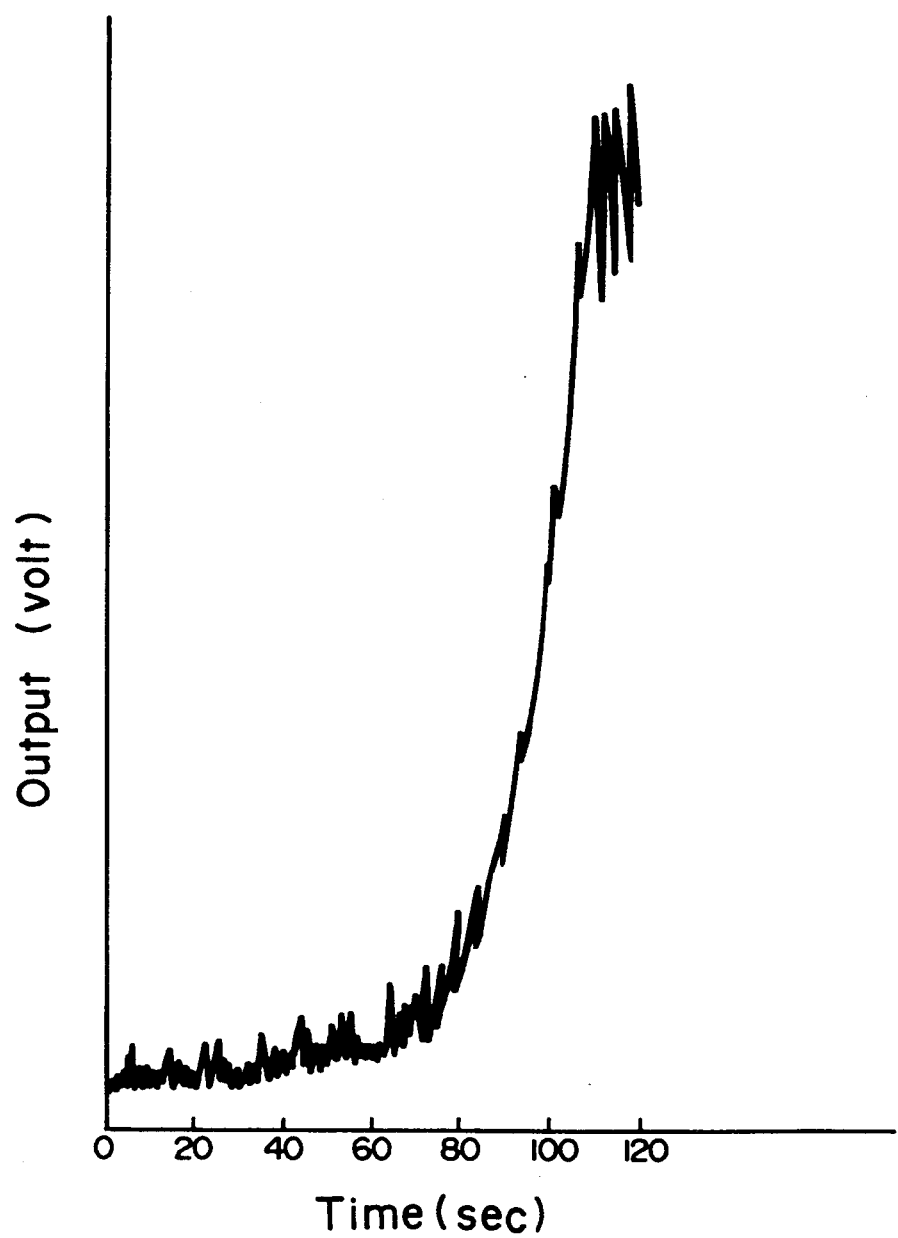
FIG. 8 is a graph indicating the results of measurement when a vegetable was cooked as in the FIG. 7 example.

FIG. 8 is an example of the actual measurements. This measurement output (voltage) as indicated in FIG. 5B was recorded by a pen recorder. When the cauliflower was being heated using the electronic circuit described in FIG. 5A inside the microwave oven shown in FIG. 7. A large variance amount was achieved in an increment within seconds.

The example shown in FIGS. 2A and 2B is given to determine the absolute humidity value, and the difference in propagation velocities of ultrasonic waves between the interior and exterior of hollow material 51. Small holes 53 were drilled in order to achieve the task, and hollow material 52 in exactly the same shape as 51 with the exception of the small holes and 51 making contact was secured with band 65, made of a thin aluminum plate with high heat conductivity in order to equally conduct the ambient temperature changes to both hollow materials 51 and 52. Only steam enters the interior of 52 through small holes 53. There may be a transient temperature difference between 51 and 52 due to the heat which the steam contains. However, hollow material 51 is not only in contact with 52 but also in contact with the atmosphere, and the temperature difference gradually becomes less.

As an accurate measuring method for the absolute humidity value, for example, a wet and dry bulb hygrometer with airing is available. However, it takes approximately 10 minutes to take an accurate measurement of the humidity.

In accordance with the example of the present invention, it is possible to measure the humidity within seconds if the temperature is stabilized quickly.

As an adjustment task, first, dry air is injected into the inside of hollow material 51, for example, and the saturated steam amount in −30° C. is 1 g/m$^3$ or less, and installation into aforementioned holder for generating element 56 and for receiving element 61 at a lower temperature was followed by distance calibration work similar to that of FIG. 4 aforementioned. This distance calibration was conducted by connecting hollow materials 51 and 52 separately to the electronic circuit shown in FIG. 5A, and adjusting until the voltage V6 becomes O, then sealing and securing with adhesive or the like.

Dry air is sealed inside hollow material 51 after aforementioned assembly and work, and ambient air with humidity which is the measuring object enters into hollow material 52. Furthermore, the temperatures in hollow materials 51 and 52 are equal, thus absolute humidity [g/m$^3$] can be obtained by measuring the voltage indicated in FIGS. 5A and 5B, and using the correlation which is shown in FIG. 6.

In accordance with the present invention, the physical phenomenon is directly measured and taken out as electrical signals, then humidity in the measuring air could easily be measured with a high degree of accuracy and automatically even at a distance. Therefore, it becomes possible to control using the electric signals obtained.

Because this method directly measures the basic physical phenomenon, accuracy in measurement is superior.

For example, a heated room interior on a cold winter day has very low humidity. If this humidity is measured using a dry and wet bulb hygrometer, airing for 10 minutes, a small amount of humidity which was evaporated from the hygrometer will increase the amount of humidity in the closed room, and the humidity value may be measured different from the initial humidity. On the other hand, according to the present invention, the accurate humidity is measured because no humidity is generated during the process.

When applied to a heat cooker, even if the sensor in the humidity measuring device is exposed to various types of gases and particles from food, there is no change in effect on the element of propagation velocity of ultrasonic wave in the air. Furthermore, even if the amplitude of ultrasonic waves caused a small change, there is no element which is affected by the change; consequently, there are no elongating changes in the measured values.

Furthermore, regarding the fast response time of humidity measurement, in particular, as indicated in the examples in FIGS. 1A or 3, once humidity enters inside exhaust passage 11, the humidity can be measured in an order of seconds, which enables automatic cooking at the proper temperature and length of time even when reheating cold food or cooking when requiring fine adjustments.

The reason why ultrasonic waves were employed in the present invention to measure humidity is to avoid problems associated with audible sonic waves, which are more prone to malfunction caused by a variety of surrounding sound sources and to avoid becoming a nuisance sound source where quietness is required. The present invention utilizes the phenomenon which is well known that in general, the average human being can not audit a sound of 20 kHz or higher.

In addition, only a microwave oven was given as an example for a heat cooker herein; however, the heat source is not limited to electromagnetic generators such as the Magnetron.

What is claimed is:

1. A humidity measuring device comprising a first chamber for accommodating reference air and a second chamber for accommodating air in which the humidity is to be determined, each of said chambers having a wall of an ultrasonic wave absorbable material; an ultrasonic wave generating means disposed at one end of each chamber; separate ultrasonic wave receiving means at the opposite end of each chamber in which the distance between the ultrasonic wave generating means and the ultrasonic wave receiving means in each chamber is the same; and a phase difference detecting means at the output of the ultrasonic wave receiving means of both chambers to detect any difference between the time of transmission of the ultrasonic waves in each chamber so that any difference detected can be used to provide the humidity condition in the second chamber.

2. The humidity measuring device of claim 1 wherein the chambers are cylindrical chambers.

3. The humidity measuring device of claim 1 wherein said chambers contact each other.

4. The humidity measuring device of claim 1 wherein said chambers are made of a thermally conductive material.

5. The humidity measuring device of claim 1 wherein each chamber has a separate ultrasonic wave generating means.

6. The humidity measuring device of claim 1 wherein the ultrasonic wave generating means is a piezoelectrically ultrasonic generating element.

7. The humidity measuring device of claim 1 wherein said first chamber is adapted to contain reference air sealed within said chamber and said second chamber has at least one opening to permit air to be tested for humidity to flow into and from said second chamber.

8. The humidity measuring device of claim 1 wherein said second chamber is disposed within the first chamber.

9. The humidity measuring device of claim 1 assembled in a cooker.

10. The humidity measuring device of claim 9 wherein said cooker has an exhaust area and said device is positional within said exhaust area.

11. The humidity measuring device of claim 9 wherein the chambers are cylindrical chambers.

12. The humidity measuring device of claim 9 wherein said chambers contact each other.

13. The humidity measuring device of claim 9 wherein said chambers are made of a thermally conductive material.

14. The humidity measuring device of claim 9 wherein each chamber has a separate ultrasonic wave generating means.

15. The humidity measuring device of claim 9 wherein the ultrasonic wave generating means is a piezoelectrically ultrasonic generating element.

16. The humidity measuring device of claim 9 wherein said second chamber is disposed within the first chamber.

17. The humidity measuring device of claim 1 wherein said phase difference detecting means comprises two comparator means and an OR gate.

* * * * *